US009439931B2

(12) United States Patent
Oh et al.

(10) Patent No.: US 9,439,931 B2
(45) Date of Patent: Sep. 13, 2016

(54) ADMINISTERING UMBILICAL CORD BLOOD-DERIVED MESENCHYMAL STEM CELLS TO TREAT NERVE INJURY

(71) Applicant: Medipost Co., Ltd., Seoul (KR)

(72) Inventors: Wonil Oh, Seoul (KR); Yoon-Sun Yang, Seoul (KR); Jong Wook Chang, Seoul (KR); Soo Jin Choi, Seoul (KR); Ju-Yeon Kim, Seoul (KR)

(73) Assignee: MEDIPOST CO., LTD, Seoul (KR)

( * ) Notice: Subject to any disclaimer, the term of this patent is extended or adjusted under 35 U.S.C. 154(b) by 228 days.

(21) Appl. No.: 13/970,074

(22) Filed: Aug. 19, 2013

(65) Prior Publication Data
US 2013/0330306 A1 Dec. 12, 2013

Related U.S. Application Data

(62) Division of application No. 12/516,913, filed as application No. PCT/KR2007/006084 on Nov. 29, 2007, now Pat. No. 9,387,226.

(60) Provisional application No. 60/867,875, filed on Nov. 30, 2006.

(30) Foreign Application Priority Data

Dec. 1, 2006  (KR) ........................ 10-2006-0120479

(51) Int. Cl.
    A01N 63/00    (2006.01)
    A01N 65/00    (2009.01)
    A61K 35/51    (2015.01)
    C12N 5/0797   (2010.01)
    A61K 45/06    (2006.01)
    C12N 5/0789   (2010.01)
    A61K 9/00     (2006.01)
    A61K 35/50    (2015.01)
    A61K 35/28    (2015.01)

(52) U.S. Cl.
    CPC ............... A61K 35/51 (2013.01); A61K 45/06 (2013.01); C12N 5/0623 (2013.01); A61K 9/0019 (2013.01); A61K 35/28 (2013.01); A61K 35/50 (2013.01); A61K 2300/00 (2013.01); C12N 5/0647 (2013.01); C12N 2501/01 (2013.01); C12N 2501/11 (2013.01); C12N 2501/115 (2013.01); C12N 2502/03 (2013.01); C12N 2502/1358 (2013.01)

(58) Field of Classification Search
    CPC ............ C12N 5/0623; C12N 2501/1358; C12N 5/0647; C12N 2506/1353; C12N 5/0663; C12N 2502/08; C12N 2501/01; C12N 2501/11; C12N 2501/115; C12N 2502/03; C12N 2502/1358; A61K 35/28; A61K 35/12; A61K 35/30; A61K 35/50; A61K 35/51; A61K 38/18; A61K 38/185; A61K 9/0019; A61K 45/06; A61K 2300/00
    See application file for complete search history.

(56) References Cited

U.S. PATENT DOCUMENTS

| 5,733,542 | A  | 3/1998  | Haynesworth et al. |
| 5,837,576 | A  | 11/1998 | Chen et al. |
| 6,372,494 | B1 | 4/2002  | Naughton et al. |
| 6,900,299 | B1 | 5/2005  | Mohapatra et al. |
| 2004/0037775 | A1 | 2/2004 | Siahaan et al. |
| 2004/0151701 | A1 | 8/2004 | Kim et al. |
| 2004/0203142 | A1 | 10/2004 | Rai |
| 2007/0037200 | A1 | 2/2007 | Ray et al. |
| 2007/0184038 | A1 | 8/2007 | Tennekoon et al. |
| 2008/0131405 | A1 | 6/2008 | Jeun |
| 2008/0249157 | A1 | 10/2008 | Cossio Mora et al. |
| 2009/0035321 | A1 | 2/2009 | Springer et al. |
| 2009/0192105 | A1 | 7/2009 | McSwiggen et al. |

FOREIGN PATENT DOCUMENTS

| EP | 1 302 534 A1 | 4/2003 |
| EP | 1 767 617 A1 | 3/2007 |
| KR | 10-2003-0069115 A | 8/2003 |
| KR | 10-2004-0016785 A | 2/2004 |
| WO | 00/53019 A1 | 9/2000 |
| WO | WO-02/36751 A2 | 5/2002 |
| WO | WO-02/086108 A1 | 10/2002 |
| WO | WO-03/070922 A1 | 8/2003 |
| WO | 2005/026343 A1 | 3/2005 |
| WO | 2007/084354 A2 | 7/2007 |
| WO | 2007/133030 A1 | 11/2007 |
| WO | 2010/056075 A2 | 5/2010 |

OTHER PUBLICATIONS

Ji et al. Interactions of Chemokines and Chemokine Receptors Mediate the Migration of Mesenchymal Stem Cells to the Impaired Site in the Brain After Hypoglossal Nerve Injury. Stem Cells, 2004, vol. 22, pp. 415-427.*
Kurozumi et al. Mesenchymal Stem Cells That Produce Neurotrophic Factors Reduce Ischemic Damage in the Rat Middle Cerebral Artery Occlusion Model. Molecular Therapy, 2005, vol. 11, pp. 96-104.*
Huang et al. Effects of Co-grafts Mesenchymal Stem Cells and Nerve Growth Factor Suspension in the Repair of Spinal Cord Injury. Journal of Huazhong Univeristy of Science and Technoloyg, 2006, vol. 26 (2), pp. 206-210.*
Hou et al. Induction of Umbilical Cord Blood Mesenchymal Stem Cells into Neuron-Like Cells In Vitro. International Journal of Hematology, 2003, vol. 78, pp. 256-261.*
Moviglia et al. Combined protocol of cell therapy for chronic spinal cord injury. Report on the electrical and functional recovery of two patients. Cytotherapy, 2006, vol. 8, 202-209.*

(Continued)

Primary Examiner — Deborah Crouch
(74) Attorney, Agent, or Firm — Sughrue Mion, PLLC

(57) ABSTRACT

A use of a composition comprising umbilical cord blood-derived mesenchymal stem cells for inducing differentiation and proliferation of neural precursor cells or neural stem cells to neural cells is provided, the composition being effective for the treatment of nerve injury diseases.

2 Claims, 8 Drawing Sheets

(56) References Cited

OTHER PUBLICATIONS

Ende et al. Parkinson's disease mice and human umbilical cord blood. J. Medicine, 2002, vol. 33, pp. 173-180.*
Quinn et al. Antioxidants in Alzheimer's disease-vitamin C delivery to a demanding brain. Journal of Alzheimer's Disease, 2003, vol. 5, pp. 309-313.*
Sun et al. Hypoxia, Ischemic Stroke, and Memory Deficits: Prospects for Therapy. IUBMB Life, 1999, vol. 48, pp. 373-378.*
Azbill et al. Impaired mitochondrial function, oxidative stress and altered antioxidant enzyme activities following traumatic spinal cord injury. Brain Research 1997, vol. 765, pp. 283-290.*
Calza et al. Neural stem cells and cholinergic neurons: Regulation by immunolesion and treatment with mitogens, retinoic acid, and nerve growth factor. PNAS, 2003, vol. 100, pp. 7325-7330.*
Chen et al. Intravenous Administration of Human Umbilical Cord Blood Reduces Behavioral Deficits After Stroke in Rats. Stroke, 2001, vol. 32, pp. 2682-2688.*
Hamilton et al. Insulin reduction of cerebral infarction due to transient focal ischemia. J. Neurosurgery, 1995, vol. 82, pp. 262-268.*
Markesbery et al. Oxidative Alterations in Neurodegenerative Diseases, Chapt. 2 in Pathogenesis of Neurodegenerative Diseases, Ed. M.P. Mattson, Humana Press Inc, Totowa, NJ, pp. 21-51.*
Moroo et al. Loss of insulin receptor immunoreactivity from the substantia nigra pars compacta neurons in Parkinson's disease. Acta Neuropathology, 1994, vol. 87, pp. 343-348.*
Tajbakhsh, S. (2009) Stem cell: what's in a name? Nature Reports Stem Cells, pp. 1-5, published online Jun. 25, 2009.
Alexanian, A.R. (2005) Neural stem cells induce bone-marrow-derived mesenchymal stem cells to generate neural stem-like cells via juxtacrine and paracrine interactions. Experimental Cell Research 310: 383-391.
Lou et al. (2003) The effect of bone marrow stromal cells on neuronal differentiation of mesencephalic neural stem cells in Sprague-Tawley rats. Brain Research 968(1): 114-121.
Jang, YK., "Mesenchymal stem cells feeder layer from human umbilical cord blood for ex vivo expanded growth and proliferation of hematopoietic progenitor cells," Ann Hematol 85(5): 343-344, May 2006.
Kadereit, S., et al., Expansion of LTC-ICs and maintenance of p21 and BCL-2 expression in cord blood CD34(+)/CD38(−) early progenitors cultured over human MSCs as a feeder layer, Stem Cells 20(6): 573-582 (2002).
Lee, Oscar, "Isolation of multipotent mesenchymal stem cells from umbilical cord blood," Blood, vol. 103, No. 5, pp. 1669-1675, Mar. 1, 2004.
Jeong, J.A. et al., "Rapid neural differentiation of human cord blood-derived mesenchymal stem cells," Neuroreport, vol. 15, No. 11, pp. 1731-1734, Aug. 6, 2004.
Chen et al., "Therapeutic Benefit of Intracerebral Transplantation of Bone Marrow Stromal Cells After Cerebral Ischemia in Rats," Journal of the Neurological Sciences, 2001, vol. 189, pp. 49-57.
Hou et al., "Induction of Umbilical Cord Blood Mesenchymal Stem Cells into Neuron-Like Cells In Vitro," International Journal of Hematology, 2003, vol. 78, pp. 256-261.
Francisco J. Rivera, et al., "Mesenchymal Stem Cells Instruct Oligodendrogenic Fate Decision on Adult Neural Stem Cells", Stem Cells, 2006, vol. 24, No. 10, pp. 2209-2219, www.StemCells.com.
Torrente et al., "Mesenchymal Stem Cell Transplantation for Neurodegenerative Diseases," Cell Transplantation, Oct. 1, 2008, vol. 17 pp. 1103-1113.
Sanberg et al., "Umbilical Cord Blood-Derived Stem Cells and Brain Repair," Ann. N.Y. Acad. Sci., 2005, vol. 1049, pp. 67-83.
Kim et al., "GDF-15 Secreted from Human Umbilical Cord Blood Mesenchymal Stem Cells Delivered Through the Cerebrospinal Fluid Promotes Hippocampal Neurogenesis and Synaptic Activity in an Alzheimer's Disease Model," Stem Cells and Development, 2015, vol. 00, No. 00, pp. 1-13.

Pesheva et al., "Galectin-3 promotes neural cell adhesion and neurite growth", Journal of Neuroscience Research, 1998, vol. 54, p. 639-654 (Abstract).
Kuklinski et al., "Expression of galectin-3 in neuronally differentiating PC12 cells is regulated both via Ras/MAPK-dependent and -independent signalling pathways", Journal of Neurochemistry, 2003, vol. 87, p. 1112-1124.
Kupershmidt et al., "The neuroprotective effect of Activin A and B: implication for neurodegenerative diseases", Journal of Neurochemistry, 2007, vol. 103, p. 962-971.
Japan Patent Office, Communication dated Jul. 7, 2015, issued in corresponding Japanese Application No. 2014-129743.
Smith et al., "Widespread Peroxynitrite-Mediated Damage in Alzheimer's Disease," Journal of Neuroscience, Apr. 15, 1997, 17(8): pp. 2653-2657.
Strelau et al., "Growth/Differentiation Factor-15/Macrophage Inhibitory Cytokine-1 is a Novel Trophic Factor for Midbrain Dopaminergic Neurons In Vivo," The Journal of Neuroscience, Dec. 1, 2000, vol. 20, No. 23, pp. 8597-8603.
Strelau et al., "Growth/differentiation factor-15 (GDF-15), a novel member of the TGF-β superfamily, promotes survival of lesioned mesencephalic dopaminergic neurons in vitro and in vivo and is induced in neurons following cortical lesioning," J Neural Transmission, 2003, 65 Suppl, pp. 197-203.
Ikehara, Susumu, "A New Concept of Stem Cell Disorders and Their New Therapy," Journal of Hematotherapy and Stem Cell Research, 2003, vol. 12, pp. 643-653.
Weiss et al., "Human Umbilical Cord Matrix Stem Cells: Preliminary Characterization and Effect of Transplantation in a Rodent Model of Parkinson's Disease," Stem Cells, Oct. 13, 2015, vol. 24(3), pp. 781-792.
Nikolic et al., "Peripherally Administered Human Umbilical Cord Blood Cells Reduce Parenchymal and Vascular β-Amyloid Deposits in Alzheimer Mice," Stem Cells and Development, Mar. 26, 2008, vol. 17 Issue 3, pp. 423-439.
Tsai et al., "G-CSF rescues the memory impairment of animal models of Alzheimer's disease," J Experimental Med., May 21, 2007, vol. 204, No. 6, pp. 1273-1280.
Zwart et al., (2008) "Analysis of Neural Potential of Human Umbilical Cord Blood-Derived Multipotent Mesenchymal Stem Cells in Response to a Range of Neurogenic Stimuli," Journal of Neuroscience Research, 86: pp. 1902-1915.
Zhou, Jin, "Co-culture system of MSCs and Aβ1-40 injured PC12 in vitro", a doctorial dissertation on Jan. 15, 2007, 72 pages.
The State Intellectual Property Office of the P.R.C., Communication dated Jan. 17, 2014, issued in corresponding Chinese Application No. 200980154402.4.
Canadian Office Action dated Nov. 25, 2013 issued in Canadian Patent Application No. 2,743,620.
Yu et al., "Induced expression of the new cytokine, activin A, in human monocytes: inhibition by glucocorticoids and retinoic acid," Immunology, 1996, vol. 88, pp. 368-374.
International Search Report mailed Sep. 20, 2012 in PCT International Application No. PCT/KR2012/000788, filed Feb. 1, 2012.
C.J. Westmark, "What's hAPPening at synapses? The role of amyloid β-protein precursor and β-amyloid in neurological disorders," Molecular Psychiatry, 2013, vol. 18, pp. 425-434.
E. Blom et al., "Rapid Progression from Mild Cognitive Impairment to Alzheimer's Disease in Subjects with Elevated Levels of Tau in Cerebrospinal Fluid and the APOE e4/e4 Genotype," Dement Geriatr Cogn Discord, May 7, 2009, vol. 27, pp. 458-464.
G. Alves et al., "CSF amyloid-β and tau proteins, and cognitive performance, in early and untreated Parkinson's Disease: the Norwegian ParkWest Study," J Neurol Neurosurg Psychiatry, 2010, vol. 81, pp. 1080-1086.
I. Mackenzie et al., "Senile plaques in temporal lobe epilepsy," Acta Neuropathol, 1994, vol. 87, pp. 504-510.
B. Klementiev et al., "A neural cell adhesion molecule-derived peptide reduces neuropathological signs and cognitive impairment induced by Abeta25-35," Neuroscience, 2007, Vo. 145, pp. 209-224.
D. Simmons et al., "ICAM, an adhesion ligand of LFA-1, is homologous to the neural cell adhesion molecule NCAM," Nature, 1988, vol. 331, pp. 624-627.

(56) References Cited

OTHER PUBLICATIONS

International Search Report mailed Aug. 9, 2010 in PCT International Application No. PCT/KR2009/006712, filed Nov. 16, 2009.
International Preliminary Report on Patentability mailed May 17, 2011 in PCT International Application No. PCT/KR2009/006712, filed Nov. 16, 2009.
G. Bowman et al., "Alzheimer's disease and the blood-brain barrier: past, present and future." Aging Health, 2008, vol. 4(1), pp. 47-55.
International Written Opinion prepared by Hungarian Intellectual Patent Office mailed Oct. 18, 2012 in Singapore Application No. 201103411-3.
Second Office Action issued by the State Intellectual Patent Office of the People's Republic of China on Feb. 5, 2013 in Chinese Application No. 200980154402.4.
Bantubungi et al., (2007) "Stem cell factor and mesenchymal and neural stem cell transplantation in a rat model of Huntington's Disease," Molecular and Cellular Neurosciences, 37(3): 454-470.
Cho Y. H. et al., (2006) "The behavioral effect of human mesenchymal stem cell transplantation in cold brain injured rats," Acta Neutochirurgica. Supplement, 99: 125-132.
Search Report dated Apr. 15, 2013 for European Patent Application No. 09 826 307.2.
N. Liu et al., "Protective Effect of Activin A to the Injury of PC12 Cells Induced by Paraquat," Chinese Journal of Clinical Neuroscience, vol. 14, No. 1, 2006, pp. 25-32.
E. Sadot, et al., "Short- and ling-term mechanisms of tau regulation in PC12 cells," Journal of Cell Science, vol. 108, 1995, pp. 2857-2864.
J. Zhou, et al., "The co-culture system of MSCs and injured PC12 in vitro could inhibit the apoptosis of PC12," Chin. J. Neurol, Jul. 2006, vol. 39, No. 7, pp. 481-484.
L. Yi-Zhao, et al., "Autologous bone mesenchymal stem cell transplantation for Alzheimer's disease in 4 cases," Journal of Clinical Rehabilitative Tissue Engineering Research, Oct. 21, 2008, vol. 12, No. 43, pp. 8431-8433.
Schindowski et al., "Regulation of GDF-15, a distant TGF-13 superfamily member, in a mouse model of cerebral ischemia," Cell Tissue Res, 2011, 343:399-409.
Ende et al., "Human Umbilical Cord Blood Cells Ameliorate Alzheimer's Disease in Transgenic Mice," Journal of Medicine, 2004, vol. 32, Nos. 3&4 pp. 241-247.
Yang, et al., "Mesenchymal stem/progenitor cells developed in cultures from UC blood," Cytotherapy, 2004, vol. 6, No. 5, pp. 476-486.
Iijima-Ando, Kanae, et al., "Overexpression of Neprilysin Reduces Alzheimer Amyloid-$\beta$42 (A$\beta$42)- induced Neuron Loss and Intraneuronal A$\beta$42 Deposits but Causes a Reduction in cAMP-respoinsive Element-binding Protein-medicated Transcription, Age-dependent Axon Pathology, and Premature Death in *Drosophila*," Journal of Biological Chemistry, Jul. 4, 2008, vol. 283, No. 27, pp. 19066-19076.
Bae, Jae-Sung, et al., "Bone Marrow-Derived Mesenchymal Stem Cells Promote Neuronal Networks with Functional Synaptic Transmission After Transplantation into Mice with Neurodegeneration," Stem Cells, 2007, pp. 1307-1316, vol. 25.
S. Maudsley, et al., "Protein twists and turns in Alzheimer disease," Nature Medicine, Apr. 2006, vol. 12, No. 4, pp. 392-393.
M. Mattson, "Pathways towards and away from Alzheimer's disease," Nature, Aug. 5, 2004, vol. 430, pp. 631-639.
D. Kondziolka, M.D., et al., "Transplantation of cultured human neuronal cells for patients with stroke," Neurology, 2000, vol. 55, pp. 565-569.
M. Pittenger, et al., "Multilineage Potential of Adult Human Mesenchymal Stem Cells," Science, 1999, vol. 284, pp. 143-147.
L. Campos, et al., "Definition of Optimal Conditions for Collection and Cryopreservation of Umbilical Cord Hematopoietic Cells," Cryobiology, 1995, vol. 32, pp. 511-515.
K. Le Blanc, et al., "HLA expression and immunologic properties of differentiated and undifferentiated mesenchymal stem cells," Experimental Hematology, 2003, vol. 31, pp. 890-896.
HM Lazarus, et al., "Ex vivo expansion and subsequent infusion of human bone marrow-derived stromal progenitor cells (mesenchymal progenitor cells): implications for therapeutic use," Bone Marrow Transplantation, 1995, vol. 16, pp. 557-564.
Minguell et al., "Biology and clinical utilization of mesenchymal progenitor cells," Brazilian J of Med and Biol Research, 2000, 33:881-887.

\* cited by examiner (× 100)

A) Neural stem cell only

B) Neural stem cell + hUCB-MSCs (X 100)

(X 200)

ADMINISTERING UMBILICAL CORD BLOOD-DERIVED MESENCHYMAL STEM CELLS TO TREAT NERVE INJURY

This is a divisional application of copending application Ser. No. 12/516,913, filed on May 29, 2009, which is a national stage application under 35 U.S.C. §371 of PCT Application No. PCT/KR2007/006084, filed on Nov. 29, 2007, which claims the benefit of U.S. Patent Provisional Application No. 60/867,875, filed on Nov. 30, 2006, and from Korean Patent Application No. 10-2006-0120479, filed on Dec. 1, 2006, the entire contents of each of which are incorporated herein by reference in their entirety.

FIELD OF THE INVENTION

The present invention relates to a use of a composition comprising human umbilical cord blood-derived mesenchymal stem cell for inducing differentiation and proliferation of neural precursor cells or neural stem cells to neural cells.

BACKGROUND OF THE INVENTION

Stroke, Parkinson's disease, Alzheimer's disease, Pick's disease, Huntington's disease, amyotrophic lateral sclerosis, traumatic central nervous system disease and spinal cord injury disease involve dysneuria caused by injury of nerve cells, and they have been generally treated by medication or surgical operation which may severely damage normal cells.

Recently a cell replacement therapy in which normal cells are transplanted to replace destroyed or damaged cells has been recognized to be effective for such diseases, and stem cells, in particular, which can be differentiated and proliferated into desired tissues are under intense studies.

Stem cells are unspecialized cells that can be proliferated unlimitedly in the undifferentiated stage and can be differentiated into diverse tissues in response to specific stimuli.

Neural stem cells, from which neurons and/or glia such as astrocytes, oligodendrocytes and/or Schwann cells form, are also undifferentiated cells having self-reproduction potency. They differentiate into neural cells, for example neurons or glia via neural precursor cells or glia precursor cells.

Mesenchymal stem cells, which differentiate into bone, cartilage, adipose tissue, muscle, tendon, ligament, neural tissue and others, have been known to be viable for the cell replacement therapy. Mesenchymal stem cells have been obtained mainly from bone marrow, but such mesenchymal stem cells provide only limited applications due to their restrictive potency for differentiation and proliferation. Further, complicated and often painful operations composed of several steps must be conducted for such cell replacement therapy, besides the problem of finding a donor who has histocompatibility antigens identical with that of a patient to exclude graft versus host reaction during bone marrow transplantation.

In recent years, the umbilical cord blood has become a target for researchers because of its high concentrations of stem cells. A number of trials to treat blood diseases by transplanting umbilical cord blood to a patient have been conducted, and umbilical cord blood banks, which preserve umbilical cord blood in a frozen form until use, have been established for the autologous transplantation therapy.

Unlike the bone marrow, the umbilical cord blood can be obtained by a simple operation from an umbilical cord and it causes little graft versus host reaction. For these reasons, worldwide studies for clinical application of the umbilical cord blood have recently been performed.

The present inventors have also extensively studied umbilical cord blood-derived mesenchymal stem cells and found that they are capable of inducing differentiation and proliferation of neural precursor cells or neural stem cells to neural cells.

SUMMARY OF THE INVENTION

Therefore, it is an object of the present invention to provide a use of a composition comprising umbilical cord blood-derived mesenchymal stem cells for inducing differentiation and proliferation of neural precursor cells or neural stem cells to neural cells.

In accordance with another aspect of the present invention, there is provided a method for inducing differentiation and proliferation of neural precursor cells or neural stem cells to neural cells, which comprises co-culturing umbilical cord blood-derived mesenchymal stem cells with the neural precursor cells or the neural stem cells.

In accordance with a further aspect of the present invention, there is provided a composition for inducing differentiation and proliferation of neural precursor cells or neural stem cells to neural cells, comprising umbilical cord blood-derived mesenchymal stem cells as an active ingredient.

In another aspect of the invention, there is provided a method for proliferating neural precursor cells or neural stem cells, which includes bringing the neural precursor cells or neural stem cells to be in contact with umbilical cord blood-derived mesenchymal stem cells. The contact may occur in vitro by culturing the neural precursor cells or neural stem cells together with umbilical cord blood-derived mesenchymal stem cells.

According to another aspect of the invention, there is provided a method for differentiating neural precursor cells or neural stem cells into neural cells, which includes bringing the neural precursor cells or neural stem cells to be in contact with umbilical cord blood-derived mesenchymal stem cells, optionally together with an agent which is capable of differentiating the neural precursor cells or neural stem cells into neural cells. The agent may be selected from the group consisting of ascorbic acid, glia derived neurotrophic factor (GDNF), brain derived neurotrophic factor (BDNF), retinoic acid, insulin and nerve growth factor (NGF).

In another aspect of the inventive embodiment, there is provided a method for simultaneously proliferating neural precursor cells or neural stem cells and differentiating the neural precursor cells or the neural stem cells into neural cells, which includes bringing the neural precursor cells or neural stem cells to be in contact with umbilical cord blood-derived mesenchymal stem cells, optionally together with an agent which is capable of differentiating the neural precursor cells or neural stem cells into neural cells. The contact may occur in vivo by administering umbilical cord blood-derived mesenchymal stem cells, optionally together with the agent, to a nerve cell injury region of a mammal. The contact may occur in vitro by culturing the neural precursor cells or neural stem cells together with umbilical cord blood-derived mesenchymal stem cells, optionally in the presence of the agent.

According to another aspect of the invention, there is provided a method for treating a nerve injury disease, which includes administering umbilical cord blood-derived mesenchymal stem cells to a nerve cell injury region of a subject in need of treating the nerve injury disease. The method may further includes administering an agent which is selected from the group consisting of ascorbic acid, glia derived neurotrophic factor (GDNF), brain derived neurotrophic factor (BDNF), retinoic acid, insulin and nerve growth factor (NGF). The umbilical cord blood-derived mesenchymal stem cells may be administered as a culture of the umbilical cord blood-derived mesenchymal stem cells and neural precursor cells or a culture of the umbilical cord blood-derived mesenchymal stem cells and neural stem cells.

In accordance with a still further aspect of the present invention, there is provided a method for treating a nerve injury disease which comprises administering the composition to a nerve cell injury region of a subject in need of treating the nerve injury disease.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1:
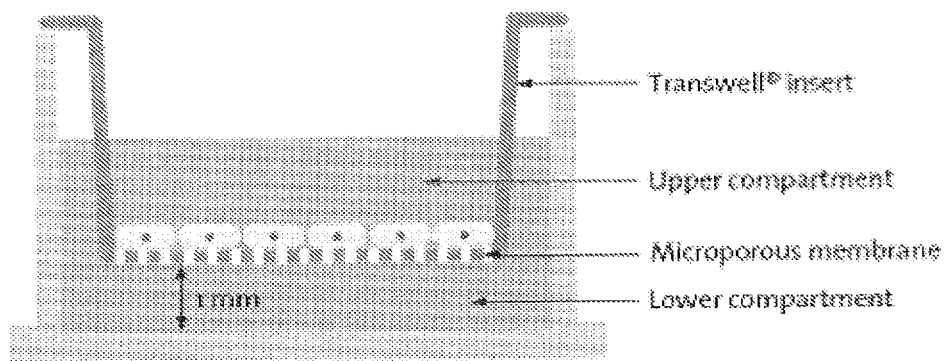
FIG. 1: a diagram of a transwell chamber used for co-culturing umbilical cord blood-derived mesenchymal stem cells and neural precursor cells.

The inventive composition for inducing differentiation and proliferation of neural precursor cells or neural stem cells to neural cells characteristically comprises umbilical cord blood-derived mesenchymal stem cells as an active ingredient.

As used herein, the term "umbilical cord blood" refers to the blood taken from the umbilical cord vein which links the placenta of a mammal with a newborn baby thereof.

The term "umbilical cord blood-derived mesenchymal stem cells" as used herein refers to mesenchymal stem cells which are isolated from the umbilical cord blood of a mammal, preferably human.

The term "a nerve injury disease" as used herein refers to a disease that accompanies, among others, behavior dysfunction due to damaged motor or sensory nerves. Exemplary nerve injury diseases include Stroke, Parkinson's disease, Alzheimer's disease, Pick's disease, Huntington's disease, amyotrophic lateral sclerosis, traumatic central nervous system disease and spinal cord injury disease.

The term "treating" refers to improving the condition, alleviating symptoms, or delaying the further progress of the disease. The term "prevention" or "inhibition" refer to preventing the manifestation of a not-yet-diagnosed disease or disorder in an animal, preferably a mammal, most preferably human, which is prone to acquire such disease or disorder; or inhibiting the development of a nerve injury disease.

The term "a neural cell" as used herein refers to a neuron of central or peripheral nervous system, and/or glia such as an astrocyte, an oligodendrocyte and/or a Schwann cell.

In isolating a monocyte comprising mesenchymal stem cells from the umbilical cord blood, a common method such as the Ficoll-Hypaque density gradient method can be employed. Specifically, said method comprises the steps of gathering umbilical cord blood from the umbilical vein after parturition till detachment of placenta; centrifuging the umbilical cord blood with a Ficoll-Hypaque gradient to obtain monocytes; and removing contaminants therefrom. The obtained monocytes may be subjected to isolation of mesenchymal stem cells therefrom, or to ultrafreezing for a long-term safekeeping till use.

The isolation of mesenchymal stem cells from the umbilical cord blood-derived monocytes may be performed by the method of Yang S E et al. (Yang S E et al., *Cytotherapy*, 6(5):476-486, 2004). Specifically, monocytes are suspended in a medium containing 5 to 30 weight %, preferably 5 to 15 weight % of fetal bovine serum (FBS), the medium including a conventional one such as DMEM, α-DMEM, Eagle's basal medium or RPMI 1640. Then, the cells in the suspension were divided into media having the same composition as described above and cultured in a 5% $CO_2$ incubator at 37° C. When the cultured cells form a mono-layer, mesenchymal stem cells having a spindle shape are observed. Then, the mesenchymal stem cells are subcultured repeatedly until the cells are sufficiently amplified.

According to the present invention, both the differentiation and proliferation of neural precursor cells or neural stem cells to neural cells can be induced by co-culturing umbilical cord blood-derived mesenchymal stem cells with neural precursor cells or neural stem cells. Namely, the umbilical cord blood-derived mesenchymal stem cells are simultaneously effective not only for inducing the differentiation of the neural precursor cells or neural stem cells to neural cells, but also for sustaining and strengthening such effects through increasing the number of the neural cells, to enhance their therapeutic effects.

Therefore, the present invention provides a use of umbilical cord blood-derived mesenchymal stem cells or a composition comprising the cells for inducing differentiation of neural precursor cells or neural stem cells to neural cells and proliferation of the resulting neural cells.

Umbilical cord blood-derived mesenchymal stem cells or a composition of comprising the cells can be used for cytotherapy of a patient suffering from a nerve injury diseases, e.g., stroke, Parkinson's disease, Alzheimer's disease, Pick's diseases, Huntington's disease, amyotrophic lateral sclerosis, traumatic central nervous system diseases and spinal cord injury disease, preferably stroke and spinal cord injury disease.

The composition of the present invention may further comprise a pharmaceutically acceptable additive.

A pharmaceutical formulation in a unit dosage form may be prepared employing the composition of the present invention according to the conventional procedures in the art. A formulation for parenteral administration such as an injection or a topical dosage form is preferable. The inventive pharmaceutical formulation may further include pharmaceutically-acceptable additives, e.g., fillers, expanders, binding agents, wetting agents, disintegrants, diluents such as surfactants and other excipients.

The inventive pharmaceutical formulation can be administered parenterally according to the conventional procedures in the art, for instance, via direct injection into an injury region as well as injection into the cerebrospinal fluid, for example, lumbar puncture and parenchymal injection, vein or artery. Preferably, it can be administered via direct injection into a peripheral or opposite region of brain or spinal cord injury region. Further, the clinical method of Douglas Kondziolka (Douglas Kondziolka, Pittsburgh, 1998) may be employed to administer the inventive pharmaceutical formulations into an injury region. Specifically, a skull of a subject is incised to make a hole having a diameter of 1 cm and a suspension of a mesenchymal stem cells in HBSS (Hank's balanced salt solution) is injected into the hole by employing a long-needle syringe and a stereotactic frame.

A typical dose of the mesenchymal stem cells may range from $1 \times 10^5$ to $1 \times 10^7$ cells/kg body weight/injection, preferably from $5 \times 10^5$ to $5 \times 10^6$ cells/kg body weight/injection, which can be administered in a single dose or in divided doses. Further, it should be understood that the amount of the effective ingredient actually administrated to a certain patient ought to be determined in light of various relevant factors including the amount of neural cells to be differentiated and proliferated, the chosen route of administration, and the body weight, age and sex of an individual patient.

The present invention also provides a method for inducing differentiation and proliferation of neural precursor cells or neural stem cells to neural cells, which comprises co-culturing umbilical cord blood-derived mesenchymal stem cells with the neural precursor cells or the neural stem cells. The co-culturing may be carried out by mixing the umbilical cord blood-derived mesenchymal stem cells with the neural precursor cells or the neural stem cells at a ratio of 1:0.1 to 1:10, preferably, 1:1 to 1:2 based on their cell number and cutting the cell mixture in a conventional cell culture medium such as DMEM, α-DMEM, α-MEM, Eagle's basal medium and RPMI 1640.

The culture medium may further comprise an antibiotic, e.g., gentamicin, and/or 5 to 15 weight % of FBS. The culture period may ranges from 5 to 10 days.

The present invention also provides a method for treating a nerve injury disease which comprises administering the umbilical cord blood-derived mesenchymal stem cell or a composition comprising the same to the nerve cell injury region of a subject in need of treating the nerve injury disease. The subject may be a mammal including human.

When administered in a therapeutically effective amount, the umbilical cord blood-derived mesenchymal stem cell induces not only differentiation of neural precursor cells or neural stem cells of central or peripheral nervous system to neural cells, but also the proliferation of the resulting neural cells, thereby resulting in the recovery of the neural functions and treatment of such nerve injury disease. The term "therapeutically effective amount" may refer to an amount which show treating or preventive effects, and may be exemplified by the amount described above. The treating effect of the umbilical cord blood-derived mesenchymal stem cell is greatly enhanced and sustained for a long time by its capability of proliferating the regenerated neural cells.

The following Examples and Test Examples are given for the purpose of illustration only, and are not intended to limit the scope of the invention.

EXAMPLE 1

Isolation and Culture of Umbilical Cord Blood-Derived Mesenchymal Stem Cells (Step 1) Acquisition of Umbilical Cord Blood (UCB)

A UCB sample was obtained from the umbilical vein of a delivering woman under her consent. Specifically, a 16-gauge needle of a UCB collection bag containing 44 ml of CPDA-1 anticoagulant (GREEN CROSS) was inserted into the umbilical vein to allow UCB to flow into the bag. The collected blood was processed within 48 hours and the cell survival rate was over 90%.

(Step 2) Isolation and Amplification of Mesenchymal Stem Cells

The UCB obtained in step 1 was subjected to centrifugation using a Ficoll-Hypaque gradient (density: 1.077 g/ml, Sigma) to obtain monocytes. The monocytes were then washed several times to remove impurities and suspended in a minimum basal medium containing 5 to 15 weight % FBS (HyClone) (α-MEM, Gibco BRL). Subsequently, a pre-measured amount of the suspension was added to the same media as above and cultured in a 5% $CO_2$ incubator at 37° C., while exchanging the media with a fresh batch of medium twice a week. When the cultured cells formed a mono-layer, the generation of mesenchymal stem cells having a spindle shape was confirmed with a microscope. The mesenchymal stem cells thus formed were subcultured repeatedly until the cells were sufficiently amplified (Yang S E et al., *Cytotherapy*, 6(5):476-486, 2004).

EXAMPLE 2

Culture of NG108-15 (NG108)

A mouse brain-derived cell, NG108-15 (Neuroblastoma X glioma hybrid) (ATCC, Cat. No. ATCC-CRL-HB-12317), having similar physiological and morphological characteristics with a neural precursor cell was cultured in DMEM (Dulbecco's modified Eagle's medium) (4 mM/L glutamine, 4.5 g/L glucose, 4.0 mg/L pyridoxin-HCl, 0.1 mM hypoxanthine-guanine, 400 nM aminopterin, 0.016 mM thymidine, 5 to 15 weight % FBS).

EXAMPLE 3

Culture of Neural Stem Cells

Neural stem cells derived from a brain cortex of a fetal mouse (Chemicon, Cat. No. SCR029) were cultured in a neural stem cell basal medium (20 ng/ml FGF-2, 20 ng/ml EGF and 2 mg/ml heparin).

EXAMPLE 4

Co-Culture of Umbilical Cord Blood-Derived Mesenchymal Stem Cells and NG108-15 (I)

The human umbilical cord blood-derived mesenchymal stem cells (hUCB-MSCs) of Example 1 were co-cultured with NG108-15 of Example 2 (hUCB-MSCs: NG108-15=1:1) employing a transwell chamber (FIG. 1) and the culture medium of Example 2. As a control group, NG108-15 was cultured alone in the culture medium of Example 2. As shown in FIG. 1, the transwell chamber was composed of lower and upper compartments which were separated from each other by a microporous membrane having 1 μm-pores. hUCB-MSCs were placed in the upper compartment, and NG108-15, in the lower compartment.

Figure 2:
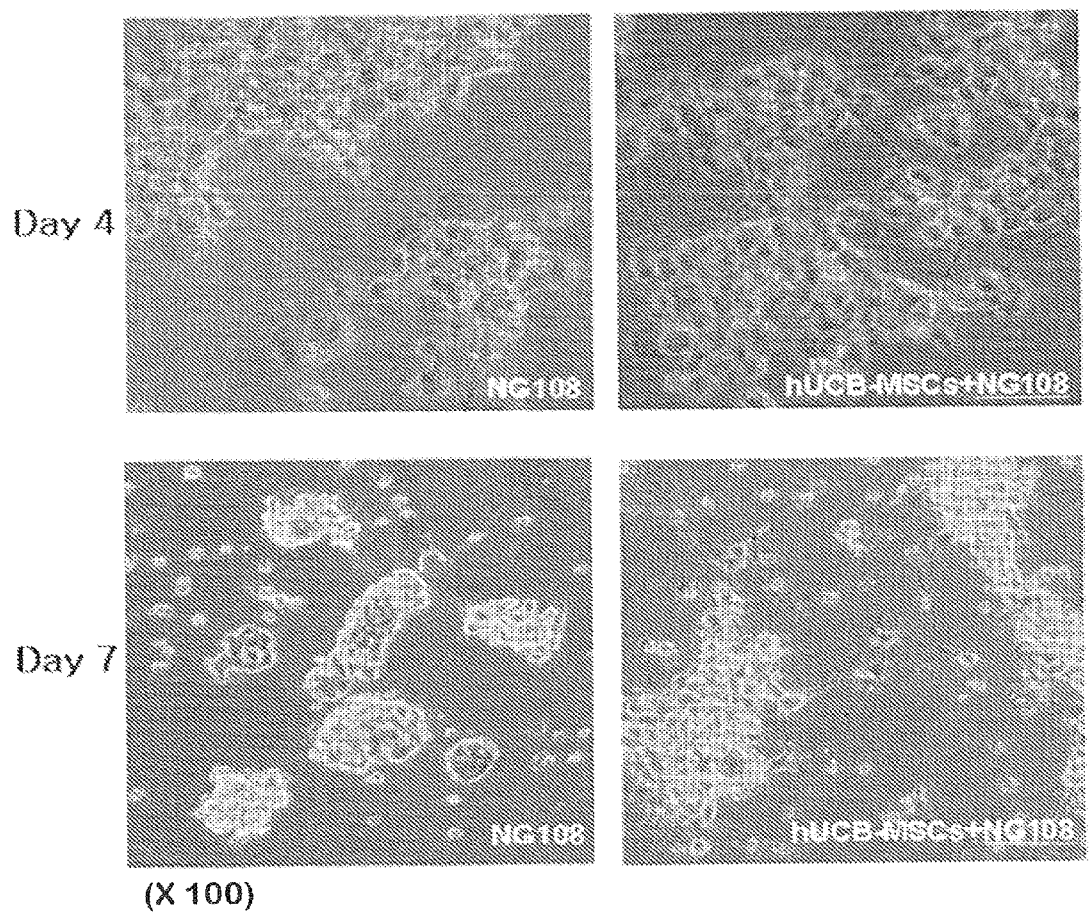
FIG. 2: photographs showing the differentiation and proliferation of NG108-15 (NG108) observed with a phase-contrast microscope (×100), 4 and 7 days after culturing NG 108-15 alone or co-culturing therewith umbilical cord blood-derived mesenchymal stem cells, respectively.

The differentiation of NG108-15 was observed with a phase-contrast microscope (×100) in 4 and 7 days. As shown in FIG. 2, NG108-15 co-cultured with hUCB-MSCs differentiated to a form of typical matured neuron-like cells in which the cells spread long branches and differentiated to have a spindle shape.

The differentiated cells were further confirmed to be neuron-like cells in 7 days employing immunostaining for tubulin-beta III, an early marker of neuronal development. Specifically, hUCB-MSCs, NG 108-15 and a mixture thereof were respectively cultured in a cover slide, and blocked by adding them to 10% normal goat serum containing 0.3% triton X-100 for 1 hour at a room temperature. The 1$^{st}$ antibody employed in the immunostaining, an anti-tubulin-beta III mouse monoclonal antibody conjugated with phycoerythrin (Chemicon), was diluted by one hundred fold with the goat serum and added thereto. The mixture was then kept overnight at 4° C., and the resulting mixture was washed three times (each time for 5 minutes) with 0.01 M PBS.

Figure 3:
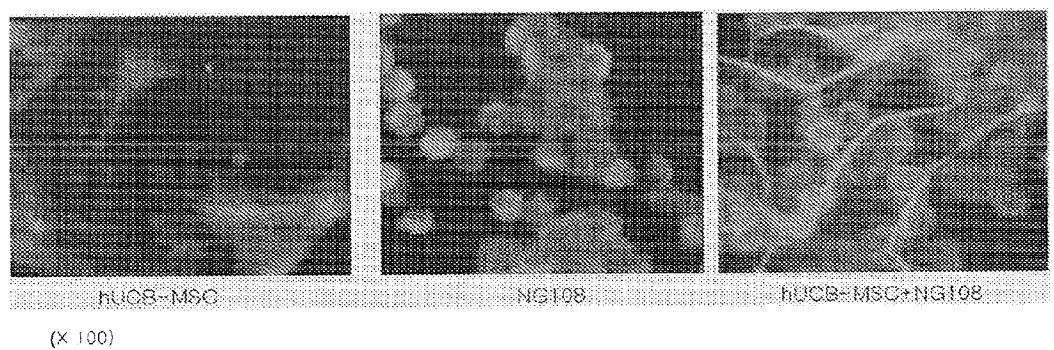
FIG. 3: photographs showing the immunostaining result for tubulin beta-III, an early marker for neuronal differentiation, 7 days after culturing NG108-15 alone or co-culturing therewith umbilical cord blood-derived mesenchymal stem cells, respectively.

As shown in FIG. 3, NG108-15 co-cultured with the mesenchymal stem cells of Example 1 exhibited a distinct response to the immunostaining for tubulin-beta III, verifying that the differentiated were neuron-like cells.

EXAMPLE 5

Co-Culture of Umbilical Cord Blood-Derived Mesenchymal Stem Cells and NG108-15 (II)

The human umbilical cord blood-derived mesenchymal stem cells were obtained by the method of Example 1 from two different individuals (hUCBMSCs-1 and hUCB-MSCs-2). NG108-15 of Example 2 was cultured alone or co-cultured with hUCB-MSCs-1 or hUCB-MSCs-2 in accordance with the method of Example 4 for 7 days. Differentiation and proliferation of the cells were observed with a phase-contrast microscope (×100).

As a comparative group, 1 mM of cAMP which induces differentiation of NG108-15 to neuron-like cells (*NeuroReport* 9, 1261-1265, 1998) was added to the culture medium of NG108-15.

Figure 4:
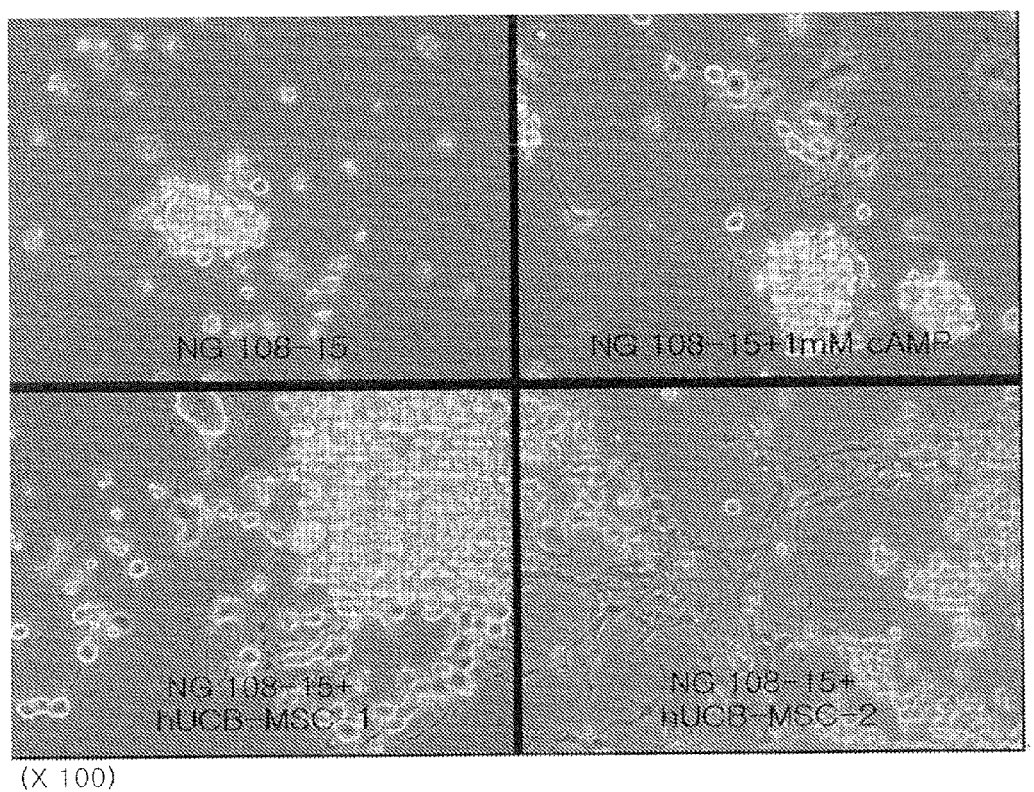
FIG. 4: photographs showing the differentiation and proliferation of NG108-15 observed with a phase-contrast microscope (×100), 7 days after culturing the NG108-15 cells alone, supplemented with cAMP or co-culturing with umbilical cord blood-derived mesenchymal stem cells obtained from two different individuals (hUCB-MSC-1 and hUCB-MSC-2), respectively.

As shown in FIG. 4, NG108-15 co-cultured with the mesenchymal stem cells was differentiated to a form of matured neuron-like cells. There was no significant difference between hUCB-MSCs-1 and hUCB-MSCs-2 in their differentiation inducing activities.

EXAMPLE 6

Co-Culture of Umbilical Cord Blood-Derived Mesenchymal Stem Cells and Neural Stem Cells (I)

The neural stem cells of Example 3 were cultured alone (control group) or co-cultured with hUCB-MSCs-1 or hUCB-MSCs-2 of Example 5 in the culture medium of Example 3, employing the transwell chamber. hUCB-MSCs were placed in the upper compartment and the neural stem cells, in the lower compartment.

hUCB-MSCs-1 and hUCB-MSCs-2 were respectively added to the medium in the concentration of 500, 1000, 2000, 4000 and 6000 cells/cm$^2$, respectively, and the neural stem cells were co-cultured with the concentration of 2000 cells/cm$^2$. The differentiation and proliferation of the cells were observed with a phase-contrast microscope (×100) (FIG. 5) in 7 days.

Figure 5:
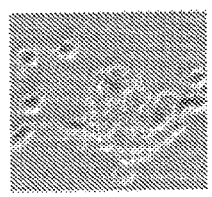
FIG. 5: photographs showing the differentiation and proliferation of neural stem cells derived from the brain cortex of a fetal mouse observed with a phase-contrast microscope (×100), 7 days after co-culturing the neural stem cells with hUCB-MSC-1 and hUCB-MSC-2 of various concentrations, respectively.
Figure 5:
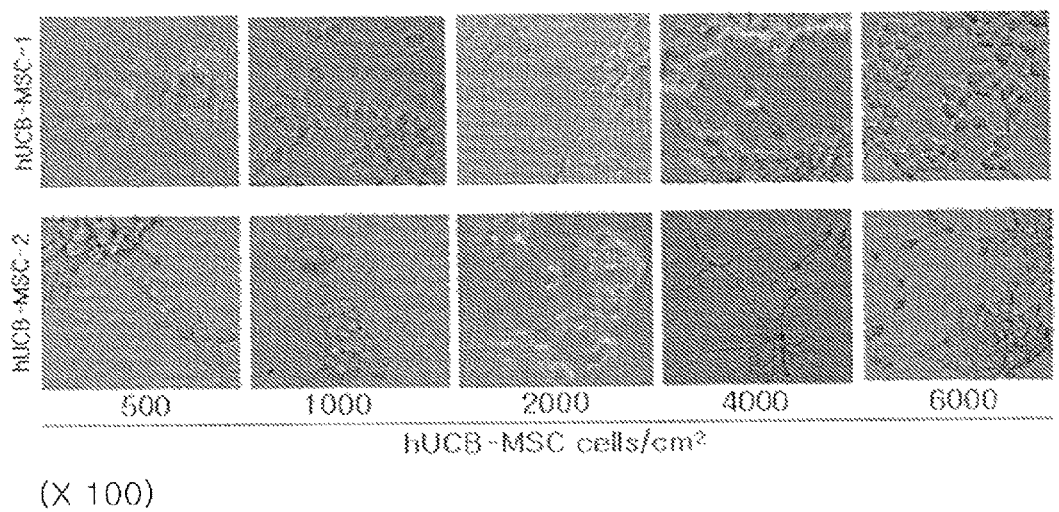

As shown in FIG. 5, the neural stem cells co-cultured with the mesenchymal stem cells were differentiated to a form of matured neurons. There was no significant difference between hUCB-MSCs-1 and hUCB-MSCs2 in their differentiation inducing activities. Further, the extent of differentiation and proliferation of the neural stem cells was directly proportional to the concentration of the mesenchymal stem cells with which co-cultured.

EXAMPLE 7

Co-Culture of Umbilical Cord Blood-Derived Mesenchymal Stem Cells and Neural Stem Cells (II)

The neural stem cells of Example 3 were cultured alone (control group) or co-cultured with hUCB-MSCs of Example 1 (hUCB-MSCs: neural stem cells=1:1) in the culture medium of Example 3, employing a transwell chamber. hUCB-MSCs were placed in the upper compartment and the neural stem cells, in the lower compartment.

Immunostaining was carried out in 4 and 7 days by employing the method of Example 4 for tubulin-beta III and microtubule-associated protein 2 (MAP2), early markers of neuronal development such that it confirmed that the differentiated were neurons.

Figure 6:
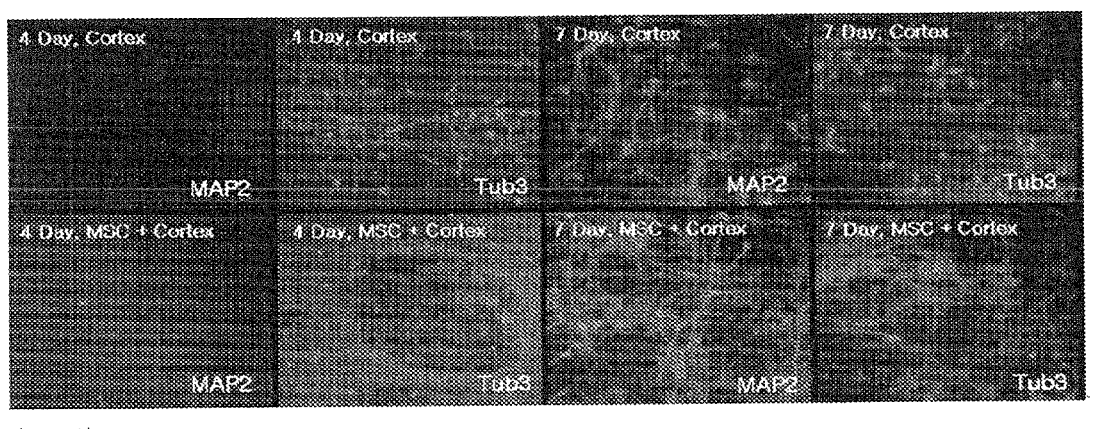
FIG. 6: photographs showing the immunostaining result for tubulin beta-III and microtubule-associated protein 2 (MAP2), early markers of neuronal differentiation, 7 days after culturing neural stem cells derived from the brain cortex of the fetal mouse alone or co-culturing therewith umbilical cord blood-derived mesenchymal stem cells, respectively.

As shown in FIG. 6, the neural stem cells co-cultured with the mesenchymal stem cells of Example 1 exhibited a distinct response to immunostaining for tubulin-beta III and MAP2, verifying that the differentiated were neurons.

EXAMPLE 8

Co-Culture of Umbilical Cord Blood-Derived Mesenchymal Stem Cells with Neural Precursor Cells or Neural Stem Cells NG108-15 of Example 2 was cultured alone (control group) or co-cultured with hUCB-MSCs of Example 1, and the neural stem cells of Example 3 was cultured alone (control group) or co-cultured with hUCB-MSCs-1 or hUCB-MSCs-2 of Example 5, according to the methods of Examples 4 and 6, respectively. The number of viable cells was counted in 7 days employing the trypan blue staining (FIGS. 7 and 8).

Figure 7:
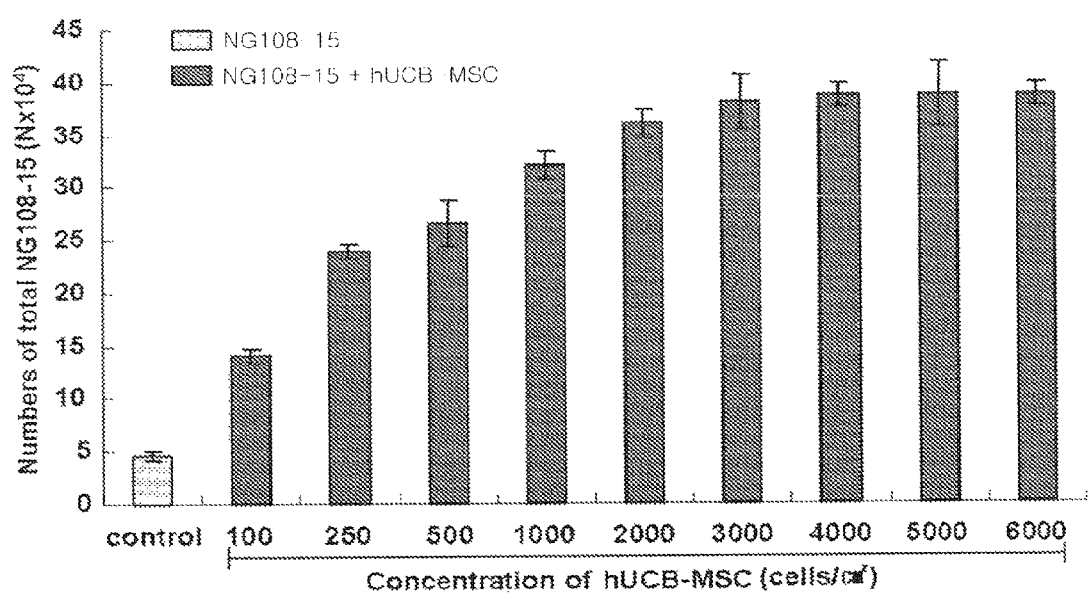
FIG. 7: a graph showing the number of viable cells assessed by the trypan blue staining, 7 days after co-culturing the NG108-15 with umbilical cord blood-derived mesenchymal stem cells of various concentrations.
Figure 8:
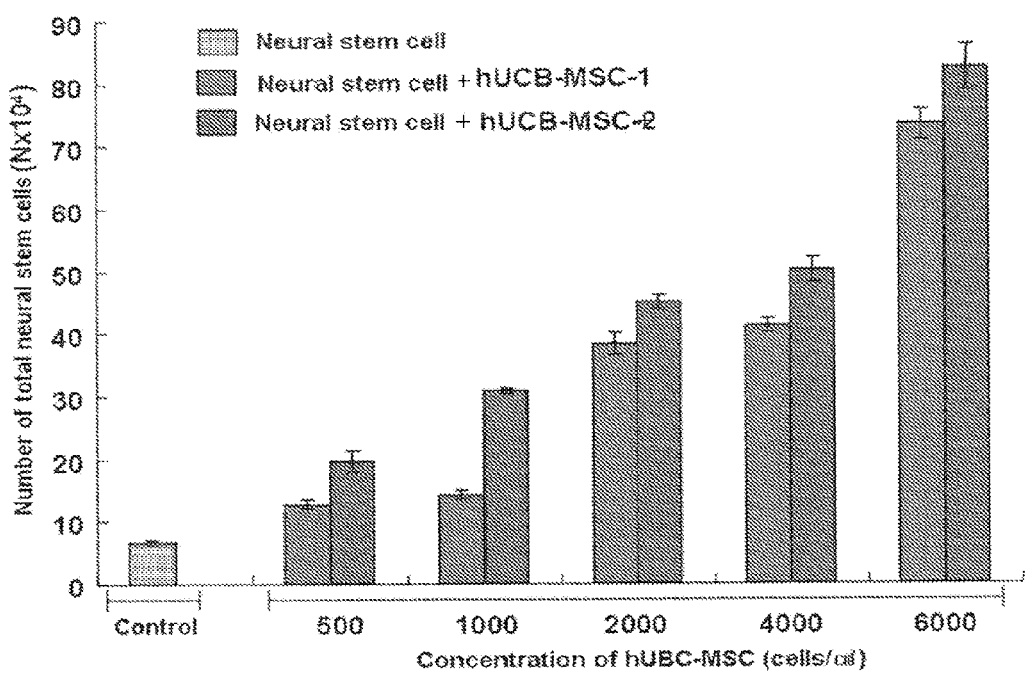
FIG. 8: a graph showing the number of viable cells assessed by the trypan blue staining, 7 days after co-culturing the neural stem cell, derived from the brain cortex of the fetal mouse, with umbilical cord blood-derived mesenchymal stem cells of various concentrations.

As shown in FIGS. 7 and 8, the numbers of NG108-15 and the neural stem cells increased in proportion to the concentration of the mesenchymal stem cells with which co-cultured, implying that the umbilical cord blood-derived mesenchymal stem cells can be simultaneously effective not only for inducing the differentiation of the neural precursor cells or neural stem cells to neural cells, but also for sustaining and strengthening such effects through increasing the number of the neural cells.

While the invention has been described with respect to the above specific embodiments, it should be recognized that various modifications and changes may be made to the invention by those skilled in the art which also fall within the scope of the invention as defined by the appended claims.

The invention claimed is:

1. A method for treating a nerve injury disease, which comprises administering umbilical cord blood-derived mesenchymal stem cells to a nerve cell injury region of a subject in need of treating the nerve injury disease, wherein the method further comprises administering an agent which is selected from the group consisting of ascorbic acid, retinoic acid, and insulin,
   wherein the umbilical cord blood-derived mesenchymal stem cells are administered as a culture of the umbilical cord blood-derived mesenchymal stem cells and neural precursor cells,
   wherein the nerve injury disease is selected from the group consisting of hypoxic ischemic brain injury, stroke, Alzheimer's disease, Pick's disease, Huntington's disease, amyotrophic lateral sclerosis and traumatic central nervous system disease, and
   wherein the administering umbilical cord blood-derived mesenchymal stem cells to a nerve cell injury region induces differentiation of neural precursor cells of the subject or neural stem cells of the subject into neural cells and proliferation of the resulting neural cells.

2. The method of claim 1, wherein the subject is a mammal.

* * * * *